(12) United States Patent
Taniguchi et al.

(10) Patent No.: US 12,311,080 B2
(45) Date of Patent: May 27, 2025

(54) CONSTRUCT HAVING STRUCTURE AND CELL MASS LINKED TOGETHER

(71) Applicant: Public University Corporation Yokohama City University, Kanagawa (JP)

(72) Inventors: Hideki Taniguchi, Yokohama (JP); Tomomi Tadokoro, Yokohama (JP)

(73) Assignee: Public University Corporation Yokohama City University, Kanagawa (JP)

( * ) Notice: Subject to any disclaimer, the term of this patent is extended or adjusted under 35 U.S.C. 154(b) by 1072 days.

(21) Appl. No.: 15/733,025

(22) PCT Filed: Oct. 26, 2018

(86) PCT No.: PCT/JP2018/039992
§ 371 (c)(1),
(2) Date: Apr. 22, 2020

(87) PCT Pub. No.: WO2019/087988
PCT Pub. Date: May 9, 2019

(65) Prior Publication Data
US 2020/0261619 A1    Aug. 20, 2020

(30) Foreign Application Priority Data

Oct. 30, 2017 (JP) .................. 2017-208853

(51) Int. Cl.
| | | |
|---|---|---|
| A61L 27/38 | (2006.01) | |
| A01K 67/0271 | (2024.01) | |
| A61L 27/40 | (2006.01) | |
| A61L 27/50 | (2006.01) | |
| C12N 5/071 | (2010.01) | |
| G01N 33/50 | (2006.01) | |

(52) U.S. Cl.
CPC .......... *A61L 27/38* (2013.01); *A01K 67/0271* (2013.01); *A61L 27/40* (2013.01); *A61L 27/507* (2013.01); *C12N 5/0672* (2013.01); *C12N 5/0677* (2013.01); *C12N 5/0697* (2013.01); *G01N 33/5008* (2013.01); *A01K 2207/12* (2013.01); *C12N 2506/45* (2013.01)

(58) Field of Classification Search
CPC .................................................. A61L 27/507
See application file for complete search history.

(56) References Cited

FOREIGN PATENT DOCUMENTS

| | | | |
|---|---|---|---|
| EP | 3026110 A1 | 6/2016 | |
| JP | 2003-503021 A | 1/2003 | |
| JP | 2009-213716 A | 9/2009 | |
| JP | 2015-23867 A | 2/2015 | |
| JP | 2016-105700 A | 6/2016 | |
| JP | 2017-127319 A | 7/2017 | |
| WO | WO-2005037226 A2 * | 4/2005 | ............. C07K 14/62 |
| WO | 2015/012158 A1 | 1/2015 | |
| WO | WO-2016108758 A1 * | 7/2016 | ............. A61K 35/12 |
| WO | 2016/141137 A1 | 9/2016 | |

OTHER PUBLICATIONS

Tamai et al., Characterization of a liver organoid tissue composed of Tissue engineering. Part A, (Nov. 2013) vol. 19, No. 21-22, pp. 2527-2535 (Year: 2013).*
Zhang et al, Elastomeric free-form blood vessels for interconnecting organs on chip systems. Lab on a chip, (Apr. 26, 2016) vol. 16, No. 9, pp. 1579-1586 (Year: 2016).*
Feucht et al, Prefabrication of tissue engineered constructs-a viable strategy for neovascularisation—a model tested on rabbits. Journal of Tissue Engineering and Regenerative Medicine (Sep. 2012) vol. 6, Supp. SUPPL. 1, pp. 299. Abstract (Year: 2012).*
Barry et al, Uniform neural tissue models produced on synthetic hydrogels using standard culture techniques. Experimental biology and medicine (Maywood, N.J.), (Nov. 2017) vol. 242, No. 17, pp. 1679-1689. Electronic Publication Date: Jun. 9, 2017 (Year: 2017).*
Extended European Search Report issued in corresponding European Patent Application No. 18874712.5 dated Jul. 9, 2021.
Nashimoto et al., "Integrating perfusable vascular networks with a three-dimensional tissue in a microfluidic device," Integrative Biology, 9: 506-518 (2017).
Takebe et al., "Vascularized and Complex Organ Buds from Diverse Tissues via Mesenchymal Cell-Driven Condensation," Cell Stem Cell, 16: 556-565 (2015).
Takebe et al., "Vascularized and functional human liver from an iPSC-derived organ bud transplant," Nature, 499: 481-485 (2013).
Kolesky et al., "Three-dimensional bioprinting of thick vascularized tissues," PNAS, 113 (12): 3179-3184 (2016).
Sekine et al., "In vitro fabrication of functional three-dimensional tissues with perfusable blood vessels," Nature Communications, 4: 1399 (2013).
International Search Report issued in corresponding International Patent Application No. PCT/JP2018/039992 dated Jan. 29, 2019.
Miwa et al., "Development of a Hierarchically Structured Hybrid Vascular Graft Biomimicking Natural Arteries," Asaio Journal, 39: 273-277 (1993).

* cited by examiner

*Primary Examiner* — Qiuwen Mi
(74) *Attorney, Agent, or Firm* — Morgan, Lewis & Bockius LLP (57) ABSTRACT

The present invention provides a system for artificially inducing and regulating "tissue interactions" among multiple tissues. A construct for transplantation into a living body, which comprises a structure and a cell mass linked to each other, the structure being an object having a three-dimensional structure and capable of mimicking or resembling a structure and/or a function of the living body.

16 Claims, 4 Drawing Sheets

Specification includes a Sequence Listing.

Fig. 1 Fusion of hiPSC Liver Bud and Mouse Large vessel

Fig. 2 Technique for Providing hiPSC Liver Bud with Blood Vessel/Bile Duct

Fig. 3 Fusion of hiPSC Liver Bud and Artificial Blood Vessel

Fig. 4 In Vivo Functional Analysis of Large vessel-Fused Liver Bud

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
aatgttgcca agctgctga                                                    19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
cttcccttca tcccgaagtt                                                   20

<210> SEQ ID NO 3
<211> LENGTH: 23
<212> TYPE: DNA
<213> ORGANISM: Artificial Sequence
<220> FEATURE:
<223> OTHER INFORMATION: primer

<400> SEQUENCE: 3
tccttgtaag tggcttcttg aac                                               23

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
tgtactgcag agataagttt agctgac                                           27

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
cattgttccc ggtttcca                                                     18

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
cagagagacc ggctgtgg                                                     18

CONSTRUCT HAVING STRUCTURE AND CELL MASS LINKED TOGETHER

SEQUENCE LISTING SUBMISSION VIA EFS-WEB

A computer readable text file, entitled "SequenceListing.txt," created on or about Apr. 22, 2020 with a file size of about 2 kb contains the sequence listing for this application and is hereby incorporated by reference in its entirety.

TECHNICAL FIELD

The present invention relates to a construct having a structure and a cell mass linked together.

BACKGROUND ART

In various fields such as human biology, regenerative medicine, drug evaluation, etc., a technique for artificially generating organoids (organ analogues) having a three-dimensional structure and biological functions similar to those of human organs is required.

With respect to generation of organoids, generation of tissue structures based on cell-autonomous multilineage differentiation by three-dimensional culture of undifferentiated cells, as represented by preparation of embryoid bodies using embryonic stem cells (ES cells) as a starting material, has been classically carried out (Non-Patent Document No. 1: Eiraku M et al., Nature, 2011). Although reconstitution of early embryos could be achieved according to this technique, it was difficult to artificially and deliberately carry out arbitrary organogenesis while securing reproducibility. Later, toward achievement of arbitrary organogenesis, various researches have been made and they include: preparation of organoids resembling a biological epithelial structure using undifferentiated cells or mutated cells (Non-Patent Document No. 2: Sato T et al., Nature 2009); preparation of organoids having both epithelium and mesenchyme (Non-Patent Document No. 3: Spence JR et al., Nature, 2011); preparation of organoids which have an internal vascular network (Non-Patent Document No. 4: Takebe T et al., Nature, 2013; Non-Patent Document No. 5: Takebe T et al., Cell Stem Cell, 2015; Patent Document No. 1: WO2013/047639); and so forth. Thus, a method of inducing and regulating self-organization using cell-cell interactions is now being established.

On the other hand, the limit of such inducing and regulating self-organization using cell-cell interactions is now being revealed. Briefly, though it is possible to artificially reconstitute minute tissue structures such as epithelial sheet structure or capillary network, no success has been reported in reconstitution of, for example, a complicated duct structure linked structurally to an epithelial sheet or a system of large vessels thicker than arterioles or venules linked to a capillary network.

PRIOR ART LITERATURE

Non-Patent Documents

Non-Patent Document No. 1: Eiraku M et al., Nature 472, pp 51-56, 2011
Non-Patent Document No. 2: Sato T et al., Nature 459, pp 262-265, 2009
Non-Patent Document No. 3: Spence JR et al., Nature 470, pp 105-109, 2011
Non-Patent Document No. 4: Takebe T et al., Nature 499, pp 481-484, 2013
Non-Patent Document No. 5: Takebe T et al., Cell Stem Cell 16, pp 556-565, 2015

Patent Document

Patent Document No. 1: WO2013/047639

DISCLOSURE OF THE INVENTION

Problem for Solution by the Invention

In order to achieve reconstitution of a complicated duct structure linked structurally to an epithelial sheet or a system of large vessels thicker than arterioles or venules linked to a capillary network, it is extremely important to develop a system for artificially inducing and regulating not only cell-cell interactions but also "tissue interactions" among multiple tissues.

It is an object of the present invention to provide a system for artificially inducing and regulating "tissue interactions" among multiple tissues.

Means to Solve the Problem

In the transplantation of a vascularized organoid (a graft) into a living body, remodeling of the blood vessels in the organoid is necessary for the organoid to be anastomosed to blood vessels of the recipient; and it takes at least several days after transplantation before blood perfusion starts. For the purpose of inducing blood perfusion into the transplanted tissue at a still earlier stage after transplantation, the present inventors have succeeded in creating an in vitro fusion between an organoid and a vascular structure including large vessels and artificial vessels. Thus, the present invention has been achieved.

A summary of the present invention is as described below.

(1) A construct for transplantation into a living body, which comprises a structure and a cell mass linked to each other, the structure being an object having a three-dimensional structure and capable of mimicking or resembling a structure and/or a function of the living body.

(2) The construct of (1) above, wherein the structure has a luminal structure, a non-luminal structure or a combination thereof.

(3) The construct of (2) above, wherein the structure is at least one member selected from the group consisting of blood vessel, bile duct, esophagus, pancreatic duct, trachea, bronchus, bronchiole, urinary duct, oviduct, vas deferens, sweat gland, Wharton's duct, Stensen's duct, lacrimal gland, heart, nerve, cerebrum, midbrain, cerebellum, thalamus, hypothalamus, pituitary gland, bridge, medulla oblongata, eye, tongue, tooth, skin, pharynx, larynx, thymus, vocal cord, stomach, duodenum, small intestine, large intestine, rectum, anus, lung, diaphragm, liver, gallbladder, pancreas, kidney, adrenal gland, thyroid, parathyroid, spleen, bladder, testis, ovary, uterus, bone, cartilage, tendon, hair follicle, chorion, greater omentum, mucosal tissue, muscle tissue and ligament.

(4) The construct of (3) above, wherein the structure is derived from the living body.

(5) The construct of (3) above, wherein the structure is an artificial material.

(6) The construct of (2) above, wherein the structure is at least one member selected from the group consisting of a sheet-like structure, a tubular structure and a filamentous structure.

(7) The construct of any one of (1) to (6) above, wherein the cell mass comprises one type or two or more types of cells.

(8) The construct of any one of (1) to (7) above, wherein the cell mass is at least one member selected from the group consisting of organ buds, spheroids, cell aggregates and cell spheres.

(9) The construct of any one of (1) to (8) above, wherein the combination of a structure and a cell mass is at least one combination selected from the group consisting of blood vessel and organ bud; bile duct and organ bud; esophagus and organ bud; pancreatic duct and organ bud; trachea and organ bud; bronchus and organ bud; bronchiole and organ bud; urinary duct and organ bud; oviduct and organ bud; vas deferens and organ bud; sweat gland and organ bud; Wharton's duct and organ bud; Stensen's duct and organ bud; lacrimal gland and organ bud; heart and organ bud; nerve and organ bud; cerebrum and organ bud; midbrain and organ bud; cerebellum and organ bud; thalamus and organ bud; hypothalamus and organ bud; pituitary gland and organ bud; bridge and organ bud; medulla oblongata and organ bud; eye and organ bud; tongue and organ bud; tooth and organ bud; skin and organ bud; pharynx and organ bud; larynx and organ bud; thymus and organ bud; vocal cord and organ bud; stomach and organ bud; duodenum and organ bud; small intestine and organ bud; large intestine and organ bud; rectum and organ bud; anus and organ bud; lung and organ bud; diaphragm and organ bud; liver and organ bud; gallbladder and organ bud; pancreas and organ bud; kidney and organ bud; adrenal gland and organ bud; thyroid and organ bud; parathyroid and organ bud; spleen and organ bud; bladder and organ bud; testis and organ bud; ovary and organ bud; uterus and organ bud; bone and organ bud; cartilage and organ bud; tendon and organ bud; hair follicle and organ bud; chorion and organ bud; greater omentum and organ bud; mucosal tissue and organ bud; muscle tissue and organ bud; and ligament and organ bud.

(10) The construct of (9) above, wherein the organ bud is at least one member selected from the group consisting of liver bud, lung organoid, respiratory epithelial organoid, intestinal organoid, pancreatic organoid, kidney organoid, brain organoid, respiratory tract organoid, stomach organoid, thyroid organoid, thymus organoid, testis organoid, esophageal organoid, skin organoid, nerve organoid, oviduct organoid, ovary organoid, salivary gland organoid, optic vesicle organoid, optic cup organoid, bladder organoid, prostate organoid, cartilage organoid, heart organoid, bone tissue organoid, muscle tissue organoid and cancer organoid.

(11) A method of preparing a tissue or an organ, comprising transplanting the construct of any one of (1) to (10) above into a non-human animal.

(12) A method of regeneration or functional recovery of a tissue or an organ, comprising transplanting the construct of any one of (1) to (10) above into a human or a non-human animal.

(13) A method of preparing a non-human chimeric animal, comprising transplanting the construct of any one of (1) to (10) above into a non-human animal.

(14) A method of evaluating a drug, comprising using at least one member selected from the group consisting of the construct of any one of (1) to (10) above, the tissue or organ prepared by the method of (11) above and the non-human chimeric animal prepared by the method of (13) above.

(15) A composite material for regenerative medicine, comprising the construct of any one of (1) to (10) above.

(16) The composite material of (15) above for use in the preparation of a tissue or an organ.

(17) The composite material of (15) above for use in the regeneration and/or functional recovery of a tissue and/or an organ.

The present invention provides a new artificial regulatory system for "tissue interactions" among multiple organoids. The present invention also provides organ analogues or organs prepared by the artificial regulatory system. Further, the present invention provides an artificial regulatory system for "tissue interactions" between multiple organoids and a different type of structure such as large vessels, and also provides organ analogues or organs prepared by the artificial regulatory system. Still further, the present invention not only provides a regulatory system for interactions between simple biological tissues but also provides a regulatory system for interactions with artificial materials prepared with a chemical substance or a metal (as represented by polymeric materials such as artificial blood vessels). The present invention also encompasses those organ analogues or organs which are prepared by the artificial regulatory system.

The new, artificial regulatory system for "tissue interactions" among multiple organoids that is provided by the present invention is a technique entirely different from the patents of Cyfuse Biomedical K.K. (WO2008/123614, WO2014/141528 and WO2014/148647) and from the technique previously reported in Birey F et al., Nature 545, pp 54-59, 2017 under the title of "Preparation of Brain by Fusion of Pallium Organoid and Subpallium Organoid, and it therefore has an inventive step. Obviously, the providing of an artificial regulatory system for "interactions" with structures and artificial materials, as well as the providing of organ analogues or organs prepared by the artificial regulatory system have novelty. The present invention is an important technique that is an innovative development of a technology for artificially generating organoids (organ analogues) having a three-dimensional structure and biological functions similar to those of human organs.

The present specification encompasses the contents disclosed in the specification and/or drawings of Japanese Patent Application No. 2017-208853 based on which the present patent application claims priority.

Effect of the Invention

According to the present invention, there are a provided new, artificial regulatory system for "tissue interactions" among multiple organoids and an artificial regulatory system for "tissue interactions" between multiple organoids and a structure such as large vessels.

BEST MODES FOR CARRYING OUT THE INVENTION

Hereinbelow, the present invention will be described in detail.

The present invention provides a construct for transplantation into a living body, which comprises a structure and a cell mass linked to each other, the structure being an object having a three-dimensional structure and capable of mimicking or resembling a structure and/or a function of the living body.

In the present invention, the structure is an object having a three-dimensional structure and capable of mimicking or resembling a structure and/or a function of a living body. The structure may mimic or resemble the structure and/or function of all or part of a tissue and/or an organ of a living body at an in vitro stage. Alternatively, there may be no mimicking or resembling at an in vitro stage, or there may be mimicking or resembling after the structure is transplanted into a living body (that is, at an in vivo stage).

The structure and the cell mass may be derived from either the same species (allogeneic) or different species (xenogeneic).

Examples of the structure include, but are not limited to, biological tissues or organs derived from an organism that is either the same as or different from an organism from which the cell mass is derived; as well as artificial tissues and organs. The structure may have a luminal structure, a non-luminal structure or a combination thereof; and the structure may be derived from an organism or may be an artificial material. Specific examples of the structure include, but are not limited to, biological tissues and organs such as blood vessel, bile duct, esophagus, pancreatic duct, trachea, bronchus, bronchiole, urinary duct, oviduct, vas deferens, sweat gland, Wharton's duct, Stensen's duct, lacrimal gland, heart, nerve, cerebrum, midbrain, cerebellum, thalamus, hypothalamus, pituitary gland, bridge, medulla oblongata, eye, tongue, tooth, skin, pharynx, larynx, thymus, vocal cord, stomach, duodenum, small intestine, large intestine, rectum, anus, lung, diaphragm, liver, gallbladder, pancreas, kidney, adrenal gland, thyroid, parathyroid, spleen, bladder, testis, ovary, uterus, bone, cartilage, tendon, hair follicle, chorion, greater omentum, mucosal tissue, muscle tissue and ligament; and artificial tissues and organs such as artificial blood vessel, artificial trachea and cell sheet. The structure may take various shapes such as a sheet-like structure, a tubular structure and a filamentous structure. When the structure is an artificial material, it may be formed from biocompatible materials. Examples of biocompatible materials include, but are not limited to, metals (e.g., stainless steel, cobalt alloy, titanium alloy, etc.), glass, ceramic, synthetic polymers (e.g., nylon, polypropylene, polydioxanone, polylactic acid, polyethylene terephthalate, Teflon™, etc.), biological materials (e.g., silk, collagen, decellularized tissue) and the like. Further, the structure may be a cell assembly (cell mass) such as organ bud, spheroid, cell aggregate, cell sphere or a fusion of cell masses, as long as the structure is capable of mimicking or resembling a structure and/or a function of a living body.

A structure and/or a function of a living body which the structure in question is capable of mimicking or resembling is not particularly limited and may be any structure that exists in a living body or any function that occurs in a living body; non-limiting examples include the structure of all or part of tissues or organs of a living body, the action of cells or interactions between cells, the action of tissues or organs composed of cells or interactions between tissue and organ, and so forth. Further, it should be noted that the filling of defective parts of tissues or organs of a living body or the reinforcement of injured parts of tissues or organs of a living body is also encompassed in the concept of biological function. The degree of mimicking or resembling a structure and/or a function of a living body is of no importance and it may be great or small.

The cell mass may be any cell assembly such as organ buds (organoids), spheroids, cell aggregates or cell spheres. The cell mass may comprise one type of cells or two or more types of cells. Further, the cell mass may be a fusion of cell assemblies. The term "organ bud" means a structure capable of differentiating into an organ through maturing. As one example of such organ bud, WO2013/047639 discloses a method of preparing an organ bud from three types of cells which are organ cells, vascular cells (preferably, vascular endothelial cells) and undifferentiated mesenchymal cells or cells differentiated therefrom. In the present invention, organ buds prepared by this method may suitably be used. The term "organ cell" means functional cells constituting organs or undifferentiated cells which differentiate into functional cells. Examples of "undifferentiated organ cell" include, but are not limited to, cells capable of differentiating into an organ such as kidney, heart, lung, spleen, esophagus, stomach, thyroid, parathyroid, thymus, gonad, brain or spinal cord; cells capable of differentiating into an ectodermal organ such as brain, spinal cord, adrenal medulla, epidermis, hair/nail/dermal gland, sensory organ, peripheral nerve or lens; cells capable of differentiating into a mesodermal organ such as kidney, urinary duct, heart, blood, gonad, adrenal cortex, muscle, skeleton, dermis, connective tissue or mesothelium; and cells capable of differentiating into an endodermal organ such as liver, pancreas, intestinal tract, lung, thyroid, parathyroid or urinary tract. Among the terms used by those skilled in the art, the following are included in the "undifferentiated organ cell": hepatoblast, hepatic progenitor cells, hepatic precursor cells, pancreatoblast, pancreatic progenitors, pancreatic progenitor cells, pancreatic precursor cells, endocrine precursors, intestinal progenitor cells, intestinal precursor cells, intermediate mesoderm, metanephric mesenchymal precursor cells, multipotent nephron progenitor, renal progenitor cells, cardiac mesoderm, cardiovascular progenitor cells, cardiac progenitor cells (JR. Spence, et al. Nature.; 470(7332):105-9.(2011); Self, et al. EMBO J.; 25(21): 5214-5228. (2006); J. Zhang, et al. Circulation Research.; 104: e30-e41(2009); G. Lee, et al. Nature Biotechnology 25, 1468-1475 (2007)) and so on. Undifferentiated organ cells may be prepared from pluripotent stem cells such as induced pluripotent stem cells (iPS cells) or embryonic stem cells (ES cells) according to known methods. The term "vascular cell" means cells constituting blood vessels or cells capable of differentiating into such cells, and vascular cells may be either differentiated or undifferentiated. Although vascular cells may be isolated from vascular tissues such as umbilical veins, vascular cells are not limited to those isolated from vascular tissues and may be induced from totipotent or pluripotent cells (e.g., iPS cells or ES cells) by directed differentiation. As vascular cell, vascular endothelial cell is preferable. The term "vascular endothelial cell" means cells constituting vascular endothelium or cells capable of differentiating into such cells. Vascular endothelial cell may be either differentiated or undifferentiated. Among the terms used by those skilled in the art, the following are included in the "vascular endothelial cell": endothelial cells, umbilical vein endothelial cells, endothelial progenitor cells, endothelial precursor cells, vasculogenic progenitors, hemangioblast (HJ. Joo, et al. Blood. 25;118(8):2094-104 (2011)) and so on. The term "mesenchymal cell" means connective tissue cells that are mainly located in mesoderm-derived connective tissues and which form support structures for cells that function in tissues. The "mesenchymal cell" is a concept that encompasses those cells which are destined to, but are yet to, differentiate into mesenchymal cells. Mesenchymal cells may be either differentiated or undifferentiated. Among the terms used by those skilled in the art, the following are included in the "mesenchymal cell": mesenchymal stem cells, mesenchymal progenitor cells, mesenchymal cells (R. Peters, et al. PLoS One. 30; 5(12):e15689 (2010)) and so on. Mesenchymal cells may be induced from totipotent or pluripotent cells (e.g., iPS cells or ES cells) by directed differentiation. Alternatively, mesenchymal cells may be cells derived from somatic cells such as bone marrow or lipid. In the Example described later, there was used a liver bud as prepared from hepatic progenitor cells induced from iPS cells by directed differentiation, mesenchymal stem cells and umbilical vein-derived vascular endothelial cells.

Examples of the combination of a structure and a cell mass include, but are not limited to: blood vessel and organ bud; bile duct and organ bud; esophagus and organ bud; pancreatic duct and organ bud; trachea and organ bud; bronchus and organ bud; bronchiole and organ bud; urinary duct and organ bud; oviduct and organ bud; vas deferens and organ bud; sweat gland and organ bud; Wharton's duct and organ bud; Stensen's duct and organ bud; lacrimal gland and organ bud; heart and organ bud; nerve and organ bud; cerebrum and organ bud; midbrain and organ bud; cerebellum and organ bud; thalamus and organ bud; hypothalamus and organ bud; pituitary gland and organ bud; bridge and organ bud; medulla oblongata and organ bud; eye and organ bud; tongue and organ bud; tooth and organ bud; skin and organ bud; pharynx and organ bud; larynx and organ bud; thymus and organ bud; vocal cord and organ bud; stomach and organ bud; duodenum and organ bud; small intestine and organ bud; large intestine and organ bud; rectum and organ bud; anus and organ bud; lung and organ bud; diaphragm and organ bud; liver and organ bud; gallbladder and organ bud; pancreas and organ bud; kidney and organ bud; adrenal gland and organ bud; thyroid and organ bud; parathyroid and organ bud; spleen and organ bud; bladder and organ bud; testis and organ bud; ovary and organ bud; uterus and organ bud; bone and organ bud; cartilage and organ bud; tendon and organ bud; hair follicle and organ bud; chorion and organ bud; greater omentum and organ bud; mucosal tissue and organ bud; muscle tissue and organ bud; and ligament and organ bud.

Specific examples of organ bud include, but are not limited to, liver bud, lung organoid, respiratory epithelial organoid, intestinal organoid, pancreatic organoid, kidney organoid, brain organoid, respiratory tract organoid, stomach organoid, thyroid organoid, thymus organoid, testis organoid, esophageal organoid, skin organoid, nerve organoid, oviduct organoid, ovary organoid, salivary gland organoid, optic vesicle organoid, optic cup organoid, bladder organoid, prostate organoid, cartilage organoid, heart organoid, bone tissue organoid, muscle tissue organoid and cancer organoid.

In the present invention, a cell mass and a structure may be linked to each other in any manner such as assembly, aggregation, fusion, anastomosis or the like. The linkage between a cell mass and a structure may be a connection for mimicking or resembling a structure and/or a function of a living body.

The cell mass linked to the structure may preferably exhibit a function. Further, as a result of linking between the structure and the cell mass, interactions between cell masses and interactions between cell masse and structure may be enhanced, potentially improving the function of the cell mass. For instance, in a structure to which a cell mass is linked, it is expected that the cell mass will be fused with the structure together with its vascular network, whereby interactions between the cell mass and the structure are enhanced to improve the function of the cell mass linked to the structure.

Any method may be used for linking the structure and the cell mass. For example, it is possible to link the structure and the cell mass by culturing multiple cell masses which are located in close proximity to each other on a structure. Preferably, the structure has cell adhering surfaces. Alternatively, multiple cell masses may first be fused to each other and then linked to the structure. The culture period can be 1-30 days and preferably 1-10 days. After linking the structure and the cell mass, the resultant construct (the product of linkage between structure and cell mass) may be allowed to mature by culturing the same for an appropriate period (e.g., 1-30 days, preferably 5-14 days). Culture may be performed by any of the following methods, batch culture, semi-batch culture (fedbatch culture) and continuous culture (perfusion culture), with perfusion culture being preferable. Further, any of stationary culture, aeration culture, spinner culture, shaking culture or rotation culture may be used.

When the structure to which the cell mass is linked is transplanted into a human or a non-human animal, vascular networks can be formed in the transplanted structure, for example, tissue or organ and blood perfusion starts. As a result, a tissue or an organ with a highly ordered tissue structure can be generated. Examples of animals to be transplanted with the structure to which the cell mass is linked include human and non-human animals that are used, for example, as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab and the like may be enumerated. Moreover, in order to avoid immunorejection, the non-human animal as the recipient is preferably an immunodeficient animal. The site of transplantation of the structure to which the cell mass is linked may be any site as long as transplantation is possible. Specific examples of the transplantation site include, but are not limited to, the blood vessel, the intracranial space, the mesentery, the liver, the spleen, the kidney, the kidney subcapsular space, and the supraportal space. By transplanting the structure to which the cell mass is linked to a living body (human or non-human animal, etc.), it is possible to regenerate tissues or organs whose function has been lost or deteriorated. Further, if human tissues or organs are prepared in non-human animals by such transplantation, it is possible to use the human tissues or organs in drug discovery screening.

Alternatively, a construct having the structure and the cell mass linked together may be cultured in vitro to be further improved in function and the resultant product may be used as an organ analogue or an organ in human biology, regenerative medicine or drug discovery screening.

The present invention provides a method of preparing a tissue or an organ, comprising transplanting into a non-human animal a construct having a structure and a cell mass linked to each other.

The present invention also provides a method of regeneration or functional recovery of a tissue or an organ, comprising transplanting into a human or a non-human animal a construct having a structure and a cell mass linked to each other.

It is possible to prepare a non-human chimeric animal by transplanting into a non-human animal a construct having a structure and a cell mass linked to each other and engrafting the construct. Therefore, the present invention provides a method of preparing a non-human chimeric animal, comprising transplanting into a non-human animal a construct having a structure and a cell mass linked to each other. The non-human animal (e.g., mouse) transplanted with the construct having a structure and a cell mass linked to each other may mimic the physiological function of the biological species (e.g., human) from which the cell mass is derived.

Still further, the present invention provides a method of evaluating a drug, comprising using at least one member selected from the group consisting of a construct comprising a structure and a cell mass linked to each other, a tissue or an organ prepared from a construct comprising a structure and a cell mass linked to each other, and a non-human chimeric animal transplanted with a construct comprising a structure and a cell mass linked to each other. Specific examples of drug evaluation include, but are not limited to, evaluation of drug metabolism (e.g., prediction of drug metabolism profiles), evaluation of drug efficacy (e.g., screening for drugs that are effective as pharmaceuticals), toxicity evaluation, and evaluation of drug interactions.

Evaluation of drug metabolism may be performed as follows. Briefly, using a cell mass prepared from human-derived cells, a construct comprising a structure and the cell mass linked to each other, a tissue or an organ prepared from a construct comprising a structure and the cell mass linked to each other, or a non-human chimeric animal transplanted with a construct comprising a structure and the cell mass linked to each other is individually administered with a candidate compound for pharmaceuticals and the resulting biological sample is then collected and analyzed, whereby a human drug metabolism profile can be obtained. As a result, prediction of the distribution/metabolism/excretion processes of pharmaceuticals in humans—this has been extremely difficult to achieve by conventional methods—becomes possible and it is expected that the development of safe and efficacious pharmaceuticals can be greatly accelerated.

Screening for drugs that are effective as pharmaceuticals may be performed as follows. Briefly, using a cell mass prepared from human-derived cells, a construct comprising a structure and the cell mass linked to each other, a tissue or an organ prepared from a construct comprising a structure and the cell mass linked to each other or a non-human chimeric animal transplanted with a construct comprising a structure and the cell mass linked to each other is administered with a novel candidate compound for pharmaceuticals. This enables subsequent analysis. As a result, a potential is expected for achieving great improvement in the precision of drug efficacy prediction for the case of actual administration to humans, which has been unsatisfactory in conventional in vitro tests.

Evaluation of toxicity may be performed as follows. Briefly, using a cell mass prepared from human-derived cells, a construct comprising a structure and the cell mass linked to each other, a tissue or an organ prepared from a construct comprising a structure and the cell mass linked to each other or a non-human chimeric animal transplanted with a construct comprising a structure and the cell mass linked to each other is administered with a test substance and, thereafter, histological damage markers or the like are measured. This makes it possible to improve the precision of damage prediction.

Evaluation of drug interactions may be performed as follows. Briefly, a construct comprising a structure and a cell mass linked to each other, a tissue or an organ prepared from a construct comprising a structure and a cell mass linked to each other or a non-human chimeric animal transplanted with a construct comprising a structure and a cell mass linked to each other is administered with multiple drugs; then, each drug is examined for its pharmacokinetics such as distribution/metabolism/excretion processes, evaluated for its toxicity, and evaluated for its efficacy.

Further, the present invention provides a composite material for regenerative medicine, including a construct comprising a structure and a cell mass linked to each other.

This composite material of the present invention may be transplanted into a living body to prepare a tissue or an organ. Regeneration or functional recovery of a tissue or an organ is also possible by transplanting the composite material of the present invention into a living body.

Upon transplantation of the composite material of the present invention into a living body, the construct comprising a structure and a cell mass linked to each other may differentiate into a tissue or an organ with vascular networks. In such vascular networks, blood perfusion may occur. It is believed that the occurrence of blood perfusion in vascular networks enables generation of a tissue or an organ with a highly ordered tissue structure equivalent or close to the tissue structure of adult tissues.

The composite material of the present invention may comprise a tissue vascularization promoter such as FGF2, HGF or VEGF, a gelatin sponge for hemostasis to cope with the bleeding from transplantation (product name: Spongel; Astellas Pharma), and a tissue adhesive for fixing transplants such as Bolheal (Teijin Pharma), Beriplast™ (CSL Behring), TachoComb™ (CSL Behring), collagen or Matrigel™.

EXAMPLE

Hereinbelow, the present invention will be described in more detail with reference to the following Example.

Example 1

Experimental Methods

Culture of Human Induced Pluripotent Stem Cells (iPSCs)

Cell culture dishes or plates were coated with iMatrix-511 (Nippi, 0.7-0.9 µg/cm$^2$) at 37° C. for 1 hour and washed with PBS. Cryopreserved human iPSCs (TkDA3 strain and 1231A3 strain, kindly provided by the University of Tokyo and Center for iPS Cell Research & Application, Kyoto University, respectively) were soaked in warm water of 37° C. for 2 minutes and thawed under shaking with hands. Cell stock solution was suspended in 9 volumes of AK02 medium (Ajinomoto) and centrifuged at 150-200×g for 5 minutes. After removal of supernatant, cells were suspended in AK02 medium supplemented with Y-27632 (WAKO, 10 µM), and human iPSCs were seeded at densities of 0.36-1.8×10$^3$ cells/cm$^2$. The medium was changed with AK02 medium at day 1 of culture and, since then, medium change was carried out every other day. About passaging cells, human iPSCs cultured for 1 week in cell culture dishes of 10 cm in diameter were washed with PBS. Then, 2 ml of Accutase (Innovative Cell Technology) was added and cells were detached by treatment at 37° C. for 5 to 10 minutes. After addition of 2 ml of AK02 medium, cells were transferred into 15 ml tubes and centrifuged at 150-200×g for 5 minutes. Supernatant was removed and the resultant cells were suspended in AK02 medium supplemented with Y-27632 (10 µM), and human iPSCs were seeded at densities of 0.36-1.8×10$^3$ cells/cm$^2$.

Directed Differentiation From iPSC to Hepatic Progenitor Cell

Cell culture dishes or plates (Thermo Fisher Scientific) were coated with iMatrix-511 (Nippi, 0.4-0.6 µg/cm$^2$) at 37° C. for 1 hour and washed with PBS. Human iPSCs cultured for 1 week in cell culture dishes of 10 cm in diameter were washed with PBS. Then, 1 ml of Accutase was added and cells were detached by treatment at 37° C. for 5 to 10 minutes. After addition of 1 ml of AK02 medium, cells were transferred into 15 ml tubes and centrifuged at 150-200×g for 5 minutes. Supernatant was removed, and the resultant cells were suspended in RPMI medium (WAKO) supplemented with penicillin/streptomycin (Gibco, 1%), B27 (Gibco, 2%), Wnt3a (R&D, 50 ng/ml), Activin A (100 ng/ml) and Y-27632 (10 µM) and seeded in laminin-coated dishes at a density of 8.4×10$^4$cells/cm$^2$. At days 1 and 3 of culture, the medium was changed with RPMI medium supplemented with penicillin/streptomycin (1%), B27 (2%), Wnt3a (50 ng/ml), Activin A (100 ng/ml) and Sodium Butyrate (0.5 mM). At day 4 of culture, the medium was changed with RPMI medium supplemented with penicillin/streptomycin (1%), B27 (2%), Wnt3a (50 ng/ml) and Activin A (100 ng/ml). The cells at day 6 of culture were designated as endodermal cell Definitive Endoderm (DE). At days 6 and 8 of culture, the medium was changed with RPMI medium supplemented with penicillin/streptomycin (1%), B27 (2%) and basic FGF (10 ng/ml). The cells at day 10 of culture were designated as hepatic progenitor cell Hepatic Endoderm (HE).

Culture of Human Mesenchymal Stem Cells (MSCs)

Mesenchymal stem cells (hereinafter, abbreviated to MSCs; Lonza; 3-5×10$^5$ cells) suspended in MSCGM medium (Lonza) were seeded in a cell culture dish (10 cm in diameter). Medium change was carried out every three days. Seven days later, cells were washed with PBS and then 2 ml of Trypsin/EDTA (Gibco) was added. Cells were detached by treatment at 37° C. for 5 minutes. MSCGM medium (2 ml) was added and cells were transferred into 15 ml tubes, followed by centrifugation at 150-200×g for 5 minutes. After removal of supernatant, cells were suspended in HCM/EGM mixed medium and supplied for preparation of liver buds; the HCM/EGM mixed medium was such that HCM (EGF free) medium (Lonza) supplemented with FBS Gold (MP Biomedicals) 5%, HGF 10 ng/ml, Oncostatin M (R&D) 20 ng/ml and Dexamethazon 100 nM was mixed with EGM medium at 1:1.

Culture of Human Umbilical Vein Endothelial Cells (HUVECs)

Kusabira Orange-labeled human umbilical vein endothelial cells (hereinafter, abbreviated to HUVECs; Lonza; 3-5×10$^5$ cells) suspended in EGM medium (Lonza) or EGM-2 medium (Lonza) were seeded in a cell culture dish (10 cm in diameter). Medium change was carried out every three days. Seven days later, cells were washed with PBS and then 2 ml of Trypsin/EDTA (Gibco) was added. Cells were detached by treatment at 37° C. for 5 minutes t. EGM medium or EGM-2 medium (2 ml) was added and cells were transferred into 15 ml tubes, followed by centrifugation at 150-200×g for 5 minutes. After removal of supernatant, cells were suspended in the above-described HCM/EGM mixed medium and supplied for preparation of liver buds.

Preparation of Liver Buds

For preparation of iPSC liver buds, human iPSC-derived DE or human iPSC-derived DE or HE (2.3×10$^5$ cells), HUVEC (1.6×10$^5$ cells) and MSC (1.6×10$^5$ cells) were suspended in the HCM/EGM mixed medium and seeded in each well of a micro-patterned 24-well plate Elplasia RB 500 400 NA (Kuraray).

Generation of a Fusion between Liver Bud and Large Vessel/Artificial Blood Vessel/Bile Duct/Intestinal Tract Twenty-four hours after preparation of liver buds, small sized liver buds were collected from the micro-patterned well plate Elplasia RB 500 400 NA (Kuraray). On 12-well cell culture insert (Thermo Fisher Scientific) or 6-well cell culture insert (Thermo Fisher Scientific), a large vessel (mouse aorta, rat femoral artery, rat femoral vein, or human umbilical artery), a porcine bile duct, a mouse fetal intestinal tract or an artificial blood vessel (Triplex, Terumo or PTFE porous tube, Chukoh Chemical Industries) was located. Then, the collected liver buds were located so that multiple liver buds would come in close proximity to each other. Alternatively, multiple small sized liver buds may be fused together and then the resultant fusion product may be fused to a large vessel/bile duct/intestinal tract or artificial blood vessel. Microscopic images of samples were taken under a fluorescent microscope BZ-X710 (Keyence) and a confocal microscope SP5 or SP8. Liver buds fused to an artificial blood vessel were collected 9 days after fusion and subjected to quantitative RT-PCR for evaluation of their function.

Functional Evaluation of Large Vessel-Equipped Liver Bud with Quantitative RT-PCR Small sized liver buds prepared in Elplasia RB 500 400 NA (Kuraray) and fusion liver buds cultured on Cell Culture Insert (Corning) were collected at day 10 of culture. RNA was purified using PureLink RNA mini kit (Thermo Fisher Scientific). cDNA synthesis was performed using iScript cDNA Synthesis Kit (Bio-Rad). Amplification and detection of genes were performed with THUNDERBIRD Probe qPCR Mix (Takara) and LightCycler™ 480 (Roche Life Science). For normalization of gene expression, Eukaryotic 18S rRNA Endogenous Control (VIC™/MGB probe, primer limited) was used. Further, primer information is given below. hAlb, probe #27, forward primer: aatgttgccaagctgctga (SEQ ID NO: 1); reverse primer: cttccctcatcccgaagtt (SEQ ID NO: 2), hAFP, probe #61, forward primer: TCCTTGTAAGTGGCTTCTTGAAC (SEQ ID NO: 3); reverse primer: TGTACTGCAGAGATAAGTTTAGCTGAC (SEQ ID NO: 4), hCD31, probe #46, forward primer: cattgttcccggtttcca (SEQ ID NO: 5); reverse primer: cagagagaccggctgtgg (SEQ ID NO: 6).

Transplantation of Rat Femoral Blood Vessel-Equipped Liver Bud Into Rat Femoral Artery Immunodeficient rat (F344/NJcl-rnu/rnu) was purchased from Clea-Japan Com. Femoral artery was taken from another rat, and a large vessel-equipped liver bud was prepared. Under isoflurane anesthesia, the immunodeficient rat was transplanted with the large vessel-equipped liver bud in its femoral artery by end-to-end anastomosis. After transplantation, blood samples were taken every week from rat carotid artery, followed by measurement of human albumin concentration in the blood. Three weeks after transplantation, the transplant was collected and subjected to histological analysis.

Preparation of Paraffin Sections

The collected tissue was fixed in 4% paraformaldehyde/phosphate buffer (PBS) for 16 hours. After washing 3 times with PBS, the fixed tissue was dehydrated by immersing in 70% ethanol, 95% ethanol and 100% ethanol (twice), each for more than 30 minutes, under shaking. Subsequently, the tissue was immersed in 50% ethanol/xylene solution, 100% xylene solution and 100% paraffin solution (twice), each for more than 30 minutes, under shaking at 65° C. and then embedded in paraffin. The embedded tissue sample was sliced into 7-10 μm thick sections with a microtome.

Hematoxylin-Eosin Stain

Paraffin sections were deparaffinized with xylene and gradually hydrophilized with 100% ethanol, 95% ethanol, 70% ethanol and Milli-Q™ water. After washing with running water, samples were stained in hematoxylin solution for 3 to 5 minutes. After washing with running water, samples were stained in eosin solution for 2 to 5 minutes. After washing with running water, samples were dehydrated with alcohol and cleared with xylene. Subsequently, a non-aqueous mounting medium was placed on the sample, which was covered with a cover glass for inclusion.

Immunohistochemical Analysis

Paraffin sections were deparaffinized with xylene and gradually hydrophilized with 100% ethanol, 95% ethanol, 70% ethanol and Milli-Q™ water. After antigen retrieval treatment in 10 mM citrate buffer (pH 6.0) at 121° C. for 15 minutes, samples were treated in 3% hydrogen peroxide water/methanol solution for 10 minutes to inactivate endogenous peroxidase. After blocking with Blocking Ones solution (Nacalai Tesque) at room temperature for 1 hour, samples were reacted with diluted primary antibody at room temperature for 1 hour or at 4° C. for overnight. After washing 3 times with PBS, samples were reacted with HRP-conjugated or fluorescence-labeled secondary antibody at room temperature for more than 30 minutes. After reaction with the fluorescence-labeled secondary antibody, samples were washed 3 times with PBS, subjected to nuclear staining with DAPI and then included for microscopic observation. After reaction with the HRP-conjugated secondary antibody, samples were reacted with DAB reagent (Vector) for 2 to 10 minutes to conduct color development. After washing with purified water, samples were stained with hematoxylin for 3 minutes. After washing with running water for 10 minutes, samples were reacted with 0.1% Sodium Bicarbonate for 5 minutes, dehydrated with alcohol and cleared with xylene. Subsequently, a non-aqueous mounting medium was placed on the sample, which was covered with a cover glass for inclusion.

ELISA Analysis

The supernatant obtained by centrifuging blood samples from rat at 4° C. at 1,500×g for 20 minutes or the collected culture broth was subjected to ELISA analysis. Analysis was performed according to the protocol of Human Albumin ELISA Quantitation Set (Bethyl Laboratories, Inc.).

Results

The results are shown in FIGS. 1 to 4.

Fusion of Human iPSC Liver Bud and Mouse Large Vessel

Figure 1:
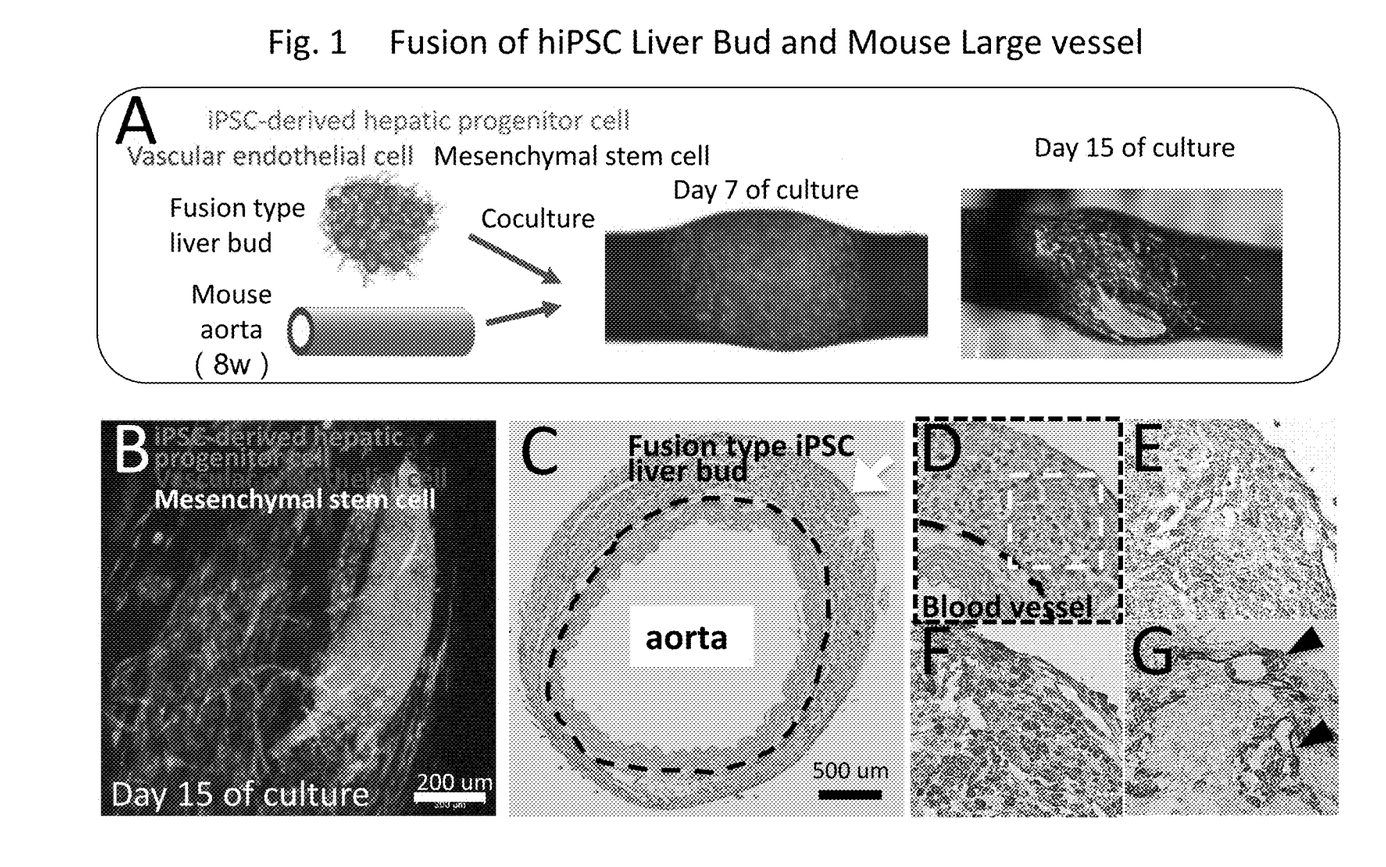
FIG. 1 Fusion of hiPSC liver bud and mouse large vessel.

Mouse large vessels were prepared from 8-week-old mice. Human iPSC liver bud (hereinafter, referred to as hiPSC liver bud) was fused to a mouse large vessel and observed chronologically. (FIG. 1A). As a result, a fusion of the hiPSC liver bud around the mouse large vessel was observed even 15 days after fusion (FIG. 1A-D). Fifteen days after fusion, formation of hiPSC liver bud-derived vascular network structure was recognized (FIG. 1B and 1G). Expression of hepatic differentiation markers such as HNF4A (FIG. 1E) and AFP (FIG. 1F) was observed in large vessel-equipped hiPSC liver bud, and human CD31 positive angiogenesis was also observed therein.

Fusion of Human iPSC Liver Bud and Blood Vessel/Bile Duct/Intestinal Tract

Figure 2:
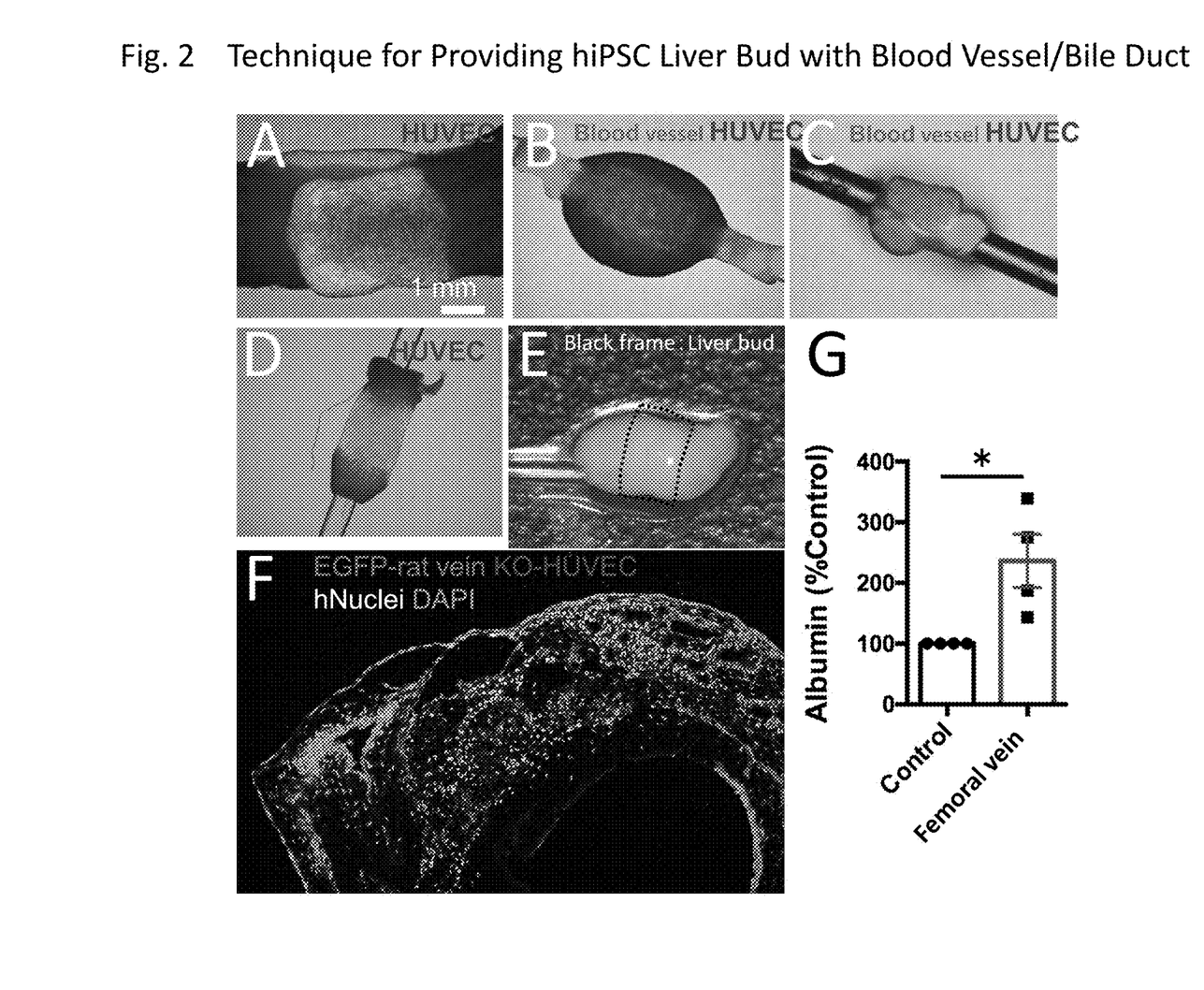
FIG. 2 Technique for providing hiPSC liver bud with blood vessels/bile duct.

It was shown that human iPSC liver bud is capable of fusing with human umbilical vein, rat femoral artery, rat femoral vein, porcine bile duct, and mouse fetal intestine to form a vascular network in the liver bud (FIG. 2 A-E). Histological analysis of rat femoral vein-equipped liver bud revealed that cells in the liver bud are human-derived and it became clear that the vascular network in the liver bud has formed a tubular structure (FIG. 2F). Rat femoral vein-equipped liver bud showed a 2.36-fold increase in secretion of human albumin relative to the secretion in a liver bud not equipped with a large vessel (FIG. 2G, n=4, p<0.03, unpaired t-test)

Fusion of Human iPSC Liver Bud and Artificial Blood Vessel

Figure 3:
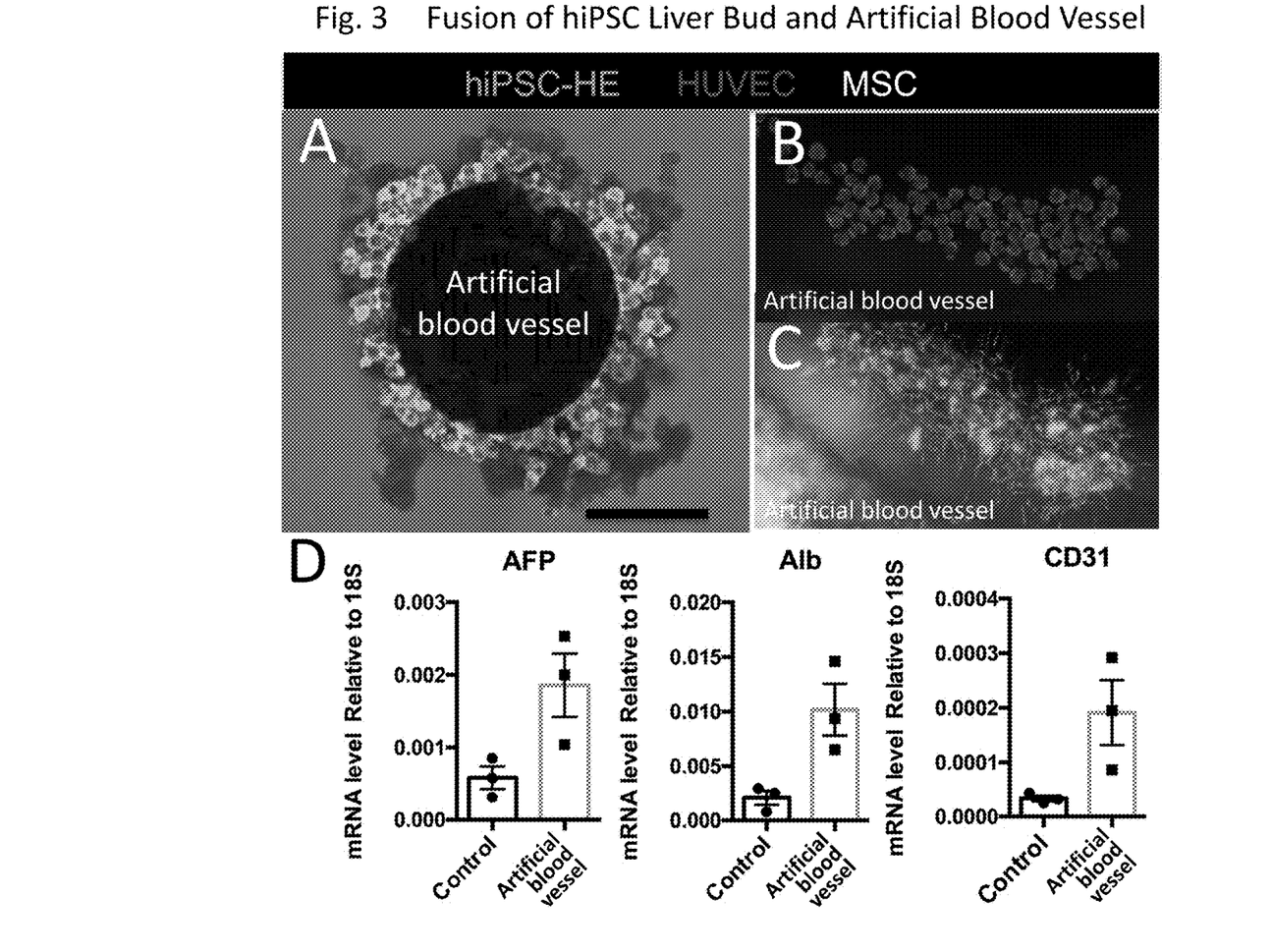
FIG. 3 Fusion of hiPSC liver bud and artificial blood vessels.

An artificial blood vessel (Triplex, Terumo or PTFE porous tube, Chukoh Chemical Industries) and liver buds were located on a cell culture insert in close proximity to each other. Then, fusion of liver buds was observed chronologically (FIG. 3A, 3B). As a result, a fusion of liver buds around the artificial blood vessel was observed 3 days after fusion and formation of a vascular network structure was recognized (FIG. 3C). Artificial blood vessel-equipped liver buds at day 10 of culture were collected and gene expression was analyzed. As a result, increases in expression of AFP, Alb and CD31 genes were recognized in artificial blood vessel-equipped liver buds relative to liver buds not equipped with a large vessel (FIG. 3D).

In Vivo Transplantation Analysis of Rat Femoral Artery-Equipped Liver Bud

Figure 4:
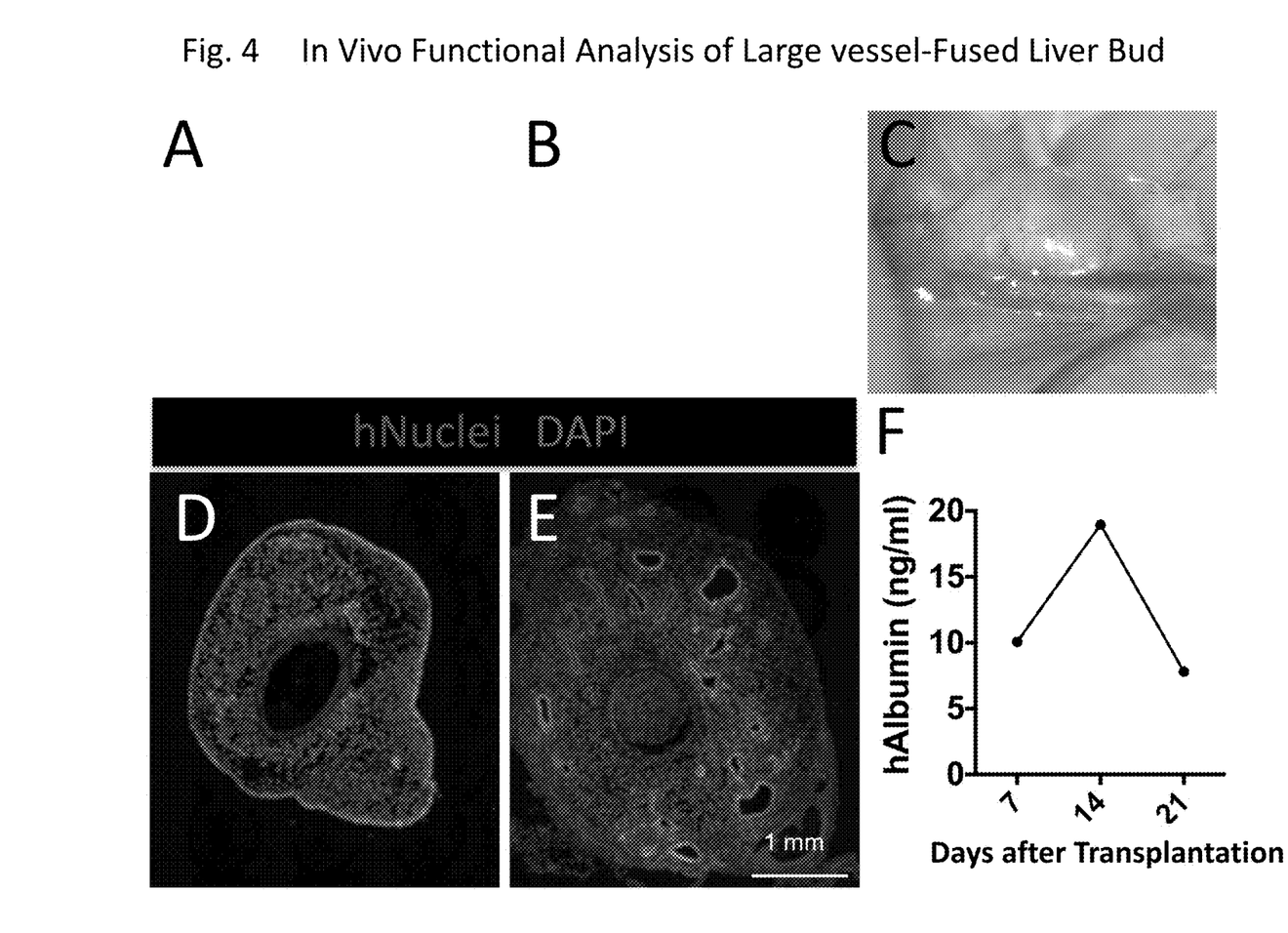
FIG. 4 In vivo functional analysis of large vessel-fused liver bud.

A rat femoral artery-equipped liver bud at day 9 to 11 of culture was transplanted into the femoral artery of immunodeficient rat (F344/NJcl-rnu/rnu) by vascular anastomosis (FIG. 4A). Before blood perfusion occurred, the liver bud was shown to present a white color but after blood perfusion, blood flew throughout the liver bud to present a red color (FIG. 4A, 4B). Engraftment of tissue was observed even 3 weeks after transplantation (FIG. 4C). The results of histological analysis of rat femoral artery-equipped liver bud before transplantation revealed the presence of abundant human tissues around the artery (FIG. 4D). Even after transplantation, the presence of abundant human tissues was also recognized around the artery (FIG. 4E). In order to measure the in vivo function of rat femoral artery-equipped liver bud, blood samples were collected from the rat chronologically, and the amount of human albumin in rat blood was measured (FIG. 4F). As a result, human albumin was detected at 7, 14 and even 21 days after transplantation, suggesting that the rat femoral artery-equipped liver bud was functioning in vivo.

All publications, patents and patent applications cited herein are incorporated herein by reference in their entirety.

INDUSTRIAL APPLICABILITY

The present invention is applicable to human biology, regenerative medicine, drug evaluation and the like.

The invention claimed is:

1. A construct for transplantation into a living body, which comprises a structure and a cell mass, the structure being an object having a three-dimensional structure and capable of mimicking or resembling a structure and/or a function of the living body,
   wherein the cell mass is fused to the structure, and a vascular network is formed from the cell mass and connected to the structure,
   wherein the cell mass comprises an organ bud and excludes skin and cartilage, and
   wherein the structure is at least one member selected from the group consisting of blood vessel, bile duct, esophagus, pancreatic duct, trachea, bronchus, bronchiole, urinary duct, oviduct, vas deferens, sweat gland, Wharton's duct, Stensen's duct, lacrimal gland, heart, nerve, cerebrum, midbrain, cerebellum, thalamus, hypothalamus, pituitary gland, bridge, medulla oblongata, eye, tongue, tooth, skin, pharynx, larynx, thymus, vocal cord, stomach, duodenum, small intestine, large intestine, rectum, anus, lung, diaphragm, liver, gallbladder, pancreas, kidney, adrenal gland, thyroid, parathyroid, spleen, bladder, testis, ovary, uterus, bone, cartilage, tendon, hair follicle, chorion, greater omentum, mucosal tissue, muscle tissue and ligament.

2. The construct of claim 1, wherein the structure has a luminal structure, a non-luminal structure, or a combination thereof.

3. The construct of claim 1, wherein the structure is derived from the living body.

4. The construct of claim 1, wherein the structure is an artificial material.

5. The construct of claim 2, wherein the structure is at least one member selected from the group consisting of sheet-like structure, a tubular structure and a filamentous structure.

6. The construct of claim 1, wherein the cell mass is organ bud.

7. The construct of claim 6, wherein the organ bud is at least one member selected from the group consisting of liver bud, lung organoid, respiratory epithelial organoid, intestinal organoid, pancreatic organoid, kidney organoid, brain organoid, respiratory tract organoid, stomach organoid, thyroid organoid, thymus organoid, testis organoid, esophageal organoid, nerve organoid, oviduct organoid, ovary organoid, salivary gland organoid, optic vesicle organoid, optic cup organoid, bladder organoid, prostate organoid, heart organoid, bone tissue organoid, muscle tissue organoid and cancer organoid.

8. The construct of claim 1, wherein the cell mass comprises more than two types of cells.

9. The construct of claim 1, wherein the cell mass is at least one member selected from the group consisting of spheroids, cell aggregates and cell spheres.

10. The construct of claim 1, wherein a combination of the structure and the cell mass is at least one combination selected from the group consisting of blood vessel and organ bud; bile duct and organ bud; esophagus and organ bud; pancreatic duct and organ bud; trachea and organ bud; bronchus and organ bud; bronchiole and organ bud; urinary duct and organ bud; oviduct and organ bud; vas deferens and organ bud; sweat gland and organ bud; Wharton's duct and organ bud; Stensen's duct and organ bud; lacrimal gland and organ bud; heart and organ bud; nerve and organ bud; cerebrum and organ bud; midbrain and organ bud; cerebellum and organ bud; thalamus and organ bud; hypothalamus and organ bud; pituitary gland and organ bud; bridge and organ bud; medulla oblongata and organ bud; eye and organ bud; tongue and organ bud; tooth and organ bud; skin and organ bud; pharynx and organ bud; larynx and organ bud; thymus and organ bud; vocal cord and organ bud; stomach and organ bud; duodenum and organ bud; small intestine and organ bud; large intestine and organ bud; rectum and organ bud; anus and organ bud; lung and organ bud; diaphragm and organ bud; liver and organ bud; gallbladder and organ bud; pancreas and organ bud; kidney and organ bud; adrenal gland and organ bud; thyroid and organ bud; parathyroid and organ bud; spleen and organ bud; bladder and organ bud; testis and organ bud; ovary and organ bud; uterus and organ bud; bone and organ bud; cartilage and organ bud; tendon and organ bud; hair follicle and organ bud; chorion and organ bud; greater omentum and organ bud; mucosal tissue and organ bud; muscle tissue and organ bud; and ligament and organ bud.

11. The construct of claim 1, wherein the organ bud is a fused organ bud.

12. A composite material for regenerative medicine, comprising the construct of claim 1.

13. A method of preparing a tissue or an organ, comprising transplanting the construct of claim 1 into a non-human animal.

14. A method of regeneration or functional recovery of a tissue or an organ, comprising transplanting the construct of claim 1 into a human or a non-human animal.

15. A method of preparing a non-human chimeric animal, comprising transplanting the construct of claim 1 into a non-human animal.

16. A method of evaluating a drug, comprising using the construct of claim 1.

* * * * *